(12) United States Patent
Kadel

(10) Patent No.: US 9,220,852 B2
(45) Date of Patent: Dec. 29, 2015

(54) METHOD FOR PRODUCING TRENCH-LIKE DEPRESSIONS IN THE SURFACE OF A WAFER

(71) Applicant: Klaus Kadel, Witten (DE)

(72) Inventor: Klaus Kadel, Witten (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 321 days.

(21) Appl. No.: 13/856,637

(22) Filed: Apr. 4, 2013

(65) Prior Publication Data

US 2013/0263847 A1  Oct. 10, 2013

(30) Foreign Application Priority Data

Apr. 10, 2012 (EP) .................... 12163650

(51) Int. Cl.
*A61M 11/02* (2006.01)
*B81C 1/00* (2006.01)

(52) U.S. Cl.
CPC ............ *A61M 11/02* (2013.01); *B81C 1/00206* (2013.01); *B81C 2201/018* (2013.01); *B81C 2201/0112* (2013.01)

(58) Field of Classification Search
CPC ..... A61M 11/02; A61M 11/00; A61M 15/00; A61M 15/0018; A61M 15/0065; A61M 16/00; A61M 31/00; A61M 31/002; A61M 5/142; A61M 5/14276; B41J 2/14; B41J 2/1433; B41J 2/16; B41J 2/1606; B41J 2/162; B41J 2/1626; B41J 2/1629; B41J 2/1631; B41J 2/1643; B41J 2/015; B41J 2/025; B41J 2/075; B41J 2/085; B41J 2/135; B41J 2/14233; B41J 2/14274; B41J 2/1612; B41J 2/1623; B41J 2/1628; B41J 2/1632; B41J 2/1634; B41J 2/1635; B41J 2/1642; B41J 2/1645; B41J 2/1646; B41J 2/175; B41J 2/17566; B81C 1/00206; A61K 9/0024; B05B 7/0012; B21D 53/02; B21D 53/04; B21D 53/045; B23P 17/00; B82Y 30/00; C08J 7/18; F02G 1/00; F02G 1/044; F02G 1/0445; F25B 39/02; F25B 39/022; F25B 9/02; F28F 21/00; F28F 3/00; F28F 3/04; F28F 3/048; F28F 3/12; G01L 15/00; G01L 19/086; G01L 7/08; G01L 9/0072; G01N 27/403; G01N 27/414; G01N 35/10; G01N 35/1016; H01G 4/40
USPC ............ 128/200.21, 200.24, 203.12, 203.15; 216/2, 27, 48, 49; 347/45, 47
See application file for complete search history.

(56) References Cited

U.S. PATENT DOCUMENTS 4,007,464 A * 2/1977 Bassous et al. ................. 347/47
4,343,013 A * 8/1982 Bader et al. .................... 347/47

(Continued)

FOREIGN PATENT DOCUMENTS

WO  9910922 A1  3/1999
WO  2006097307 A1  9/2006

OTHER PUBLICATIONS

International Search Report and Written Opinion for PCT/EP2013/057301 mailed Jul. 26, 2013.

*Primary Examiner* — Annette Dixon
(74) *Attorney, Agent, or Firm* — Michael P. Morris; Mary-Ellen M. Devlin

(57) ABSTRACT

In a method of producing trench-like depressions in the surface of a wafer, particularly a silicon wafer, by plasma etching, in which the depressions are produced by alternate passivation and etching, each depression in its final geometry is provided with a protective layer of the polytetrafluoroethylene type.

12 Claims, 3 Drawing Sheets

(56) References Cited

U.S. PATENT DOCUMENTS

| | | | |
|---|---|---|---|
| 4,392,362 A * | 7/1983 | Little | 62/51.1 |
| 4,658,269 A * | 4/1987 | Rezanka | 347/45 |
| 5,759,421 A * | 6/1998 | Takemoto et al. | 216/27 |
| 5,863,371 A * | 1/1999 | Takemoto et al. | 156/273.3 |
| 6,284,148 B1 | 9/2001 | Laermer et al. | |
| 7,267,427 B2 * | 9/2007 | Miura et al. | 347/47 |
| 7,571,722 B2 * | 8/2009 | Wuttke et al. | 128/200.14 |
| 2008/0211871 A1 * | 9/2008 | Sakurai et al. | 347/47 |
| 2008/0248253 A1 | 10/2008 | Bieber et al. | |
| 2010/0026760 A1 * | 2/2010 | Matsuo | 347/47 |
| 2011/0157277 A1 * | 6/2011 | Zhao et al. | 347/44 |

* cited by examiner

METHOD FOR PRODUCING TRENCH-LIKE DEPRESSIONS IN THE SURFACE OF A WAFER

BACKGROUND

The invention relates to a method of producing trench-like depressions in the surface of a wafer, particularly a silicon wafer or a glass wafer, by plasma etching, wherein the depressions are formed by alternate passivation and etching. The invention further relates to a micronozzle produced by the method and a nebuliser comprising a micronozzle.

For producing micronozzles for dispensing a fluid it is known to produce them from a composite of a silicon wafer and a glass plate applied thereto. In this process microporous structures or channels, which form nozzle channels in conjunction with the glass plate, are etched into the wafer surface. Alternatively, microporous structures or channels may be etched into the surface of a glass plate or a glass wafer to form nozzle channels in conjunction with a silicon wafer or another glass plate. By suitably cutting the composite consisting of silicon wafer and glass plate, micronozzles can then be cut from it by sawing. The micronozzle may comprise two or more plates, of which at least a first plate has a trench-like structure, the trenches connecting the inlet side and the nebuliser nozzle(s) provided as outlet(s) on the opposite side, while another, generally unstructured second plate is placed on the structured side of the first plate and fixedly attached thereto. A nozzle body comprising three layers may consist, for example, of a structured silicon plate, a planar silicon cover plate and a thin glass plate arranged between them.

According to DE 42 360 37 A1 a thin layer of silicon is thermally oxidised on the surface that is to be structured. The oxide layer subsequently serves as a mask for etching the trench structures. A photosensitive plastics layer is applied to this layer by centrifugation and bonded thereto. The structures are transferred into this plastics layer photo-optically by contact copying using a mask on a scale of 1:1 and developed. Alternatively, the structures may be transferred into the plastics layer by projection lithography using masks with preferably 5× magnified structures and developed. The plastics structures are used in the next process step as masking for the structuring of the silicon dioxide layer. This structuring is carried out by reactive etching with ion beams. During the structuring of the oxide layer, the plastics is removed entirely or removed after the oxide structuring or silicon structuring. The oxide layer structured in this way then acts as masking for etching the, for example, 5-7 μm deep trench structures in the silicon. At the same time the oxide layer is slowly removed. At the end of this structuring process, there are U-shaped or rectangular, box-shaped trench structures on the silicon plate, but in plan view these structures may have virtually any desired plane geometry. These etched shapes may be produced both by isotropic dry etching processes and also by isotropic wet etching processes. With anisotropically acting etching processes (both with reactive ion plasma and with wet-chemical agents) it is possible to obtain triangular nozzle cross-sections from V-shaped trench structures or trench structures with perpendicular edges of monocrystalline base plates. The geometric shapes of the trenches may also be altered by a combination of etching techniques and coating techniques. Virtually any desired geometric shapes may be obtained. After the structuring, the silicon plate is cleaned and the remaining silicon dioxide is removed by wet chemical methods.

Micronozzles of this kind are used, for example, in medical inhalers, the technical principles of which are described, for example, in WO 91/14468 or WO 97/12687. In these inhalers the amount of liquid medicament formulation to be nebulised is forced by high pressure up to 500 bar through a micronozzle with preferably two nozzle exits and thereby converted into the respirable aerosol. Reference is made expressly to the above-mentioned documents in their entirety, within the scope of the present description.

SUMMARY OF THE INVENTION

The problem of the invention is to provide a method and a micronozzle, as well as a nebuliser comprising a micronozzle, of the kind mentioned hereinbefore, which is embodied to be self-cleaning with a thin functionalising layer.

According to the invention, the problem is solved in the method by the fact that each depression, in its final geometry, is provided with a protective layer of the polytetrafluoroethylene type.

By the term "of the polytetrafluoroethylene type" are meant CFx or CxFy polymers which are conventionally used as so-called plasma polymers within the scope of a deep etching. The protective layer is chemically very unreactive and has a very low coefficient of friction together with a low surface tension. Accordingly, the substances that pass through leave no residues behind in the depressions and the micronozzle is virtually self-cleaning.

Preferably, the protective layer is formed from the plasma polymer used for the passivation and its thickness is affected by the potential applied. In the so-called Bosch process used in connection with the invention and known in the art as well as from WO 99/10922, deep etching of silicon is carried out in various partial processes, each of which is characterised by etching and passivation. First, a thin plasma polymer layer with a thickness of a few nm is deposited, which is removed at the surfaces in a subsequent physical process. Then, isotropic etching is carried out, which is in turn followed by another deposition of a plasma polymer layer for passivation of the isotropically etched areas for the next step. In the following steps the polymer layer is removed again and then the etching of the next step ensues. Whereas, in the prior art, etching and subsequent removal of the polymer are generally carried out in a final step to achieve the desired depth, according to the invention in a last step after the required depth has been achieved the plasma polymer is deposited. In order to achieve a relatively large thickness of the protective layer that far exceeds the thickness of the layer for the passivation, the potential applied is altered, compared with the preceding passivation steps, while the skilled man will be familiar with the measures required. The procedure described can also be carried out in a combined Bosch-Cyro process in which the wafer is cooled during etching.

According to one feature, the protective layer is deposited before a masking layer has been stripped off, in particular from the surface of the depressions. The stripping, i.e., removal of the masking layer from the surface also takes off the protective layer adhering to the masking layer. The masking layer may in particular comprise photoresist, $SiO_2$, $Si_3N_4$ or metal.

The gas used for the protective layer is expediently trifluoromethane ($CHF_3$), tetrafluoroethylene ($C_2F_4$), octafluorocyclobutane ($C_4F_8$) or a mixture of these gases with an inert gas.

In order to close off the depressions so as to form channels, after the stripping of a masking layer, particularly an oxide layer, the surface of the wafer comprising the depressions is attached to a glass plate by anodic bonding. The skilled man is familiar with bonding from U.S. Pat. No. 3,397,278, for example, and the glass used may be an alkali borosilicate glass, for example, which is obtainable on the market, for example, under the brand name Pyrex (#7740 Corning) or Tempax (Schott). If the depressions have been made in the surface of a glass wafer, they may obviously be closed off with a silicon plate to form channels.

Alternatively, the protective layer is deposited after the wafer has been attached to the bond glass, for which purpose the gas for the protective layer is introduced into the depressions. Therefore the application of the protective layer need not be carried out immediately after the etching but may be done in a subsequent process.

The problem on which the invention is based is further solved by a micronozzle according to one or more further embodiments herein, such as including a nebuliser.

The protective layer prevents the interaction of constituents and particles of the formulation, which are expelled through a nozzle opening of the micronozzle, with the interfaces of the depressions of the micronozzle. The free energy of the surface of the depressions that partly form the nozzle and nozzle channels, and hence its wettability, is minimised in this region, and this is associated with a reduction in the immobilisation of residues of material on the nozzle outlet, i.e., in the immediate area of the nozzle opening. When the micronozzle is used the material residues are expelled and the depressions provided with the protective layer are virtually self-cleaning.

It will be understood that the features mentioned above and still to be explained hereinafter may be used not only in the particular combination stated but also in other combinations. The scope of the invention is defined only by the claims.

BRIEF DESCRIPTION OF THE DRAWINGS

The invention is hereinafter explained more fully by means of an exemplifying embodiment with reference to the associated drawings, wherein.

DETAILED DESCRIPTION OF THE PREFERRED EMBODIMENTS

Figure 1:
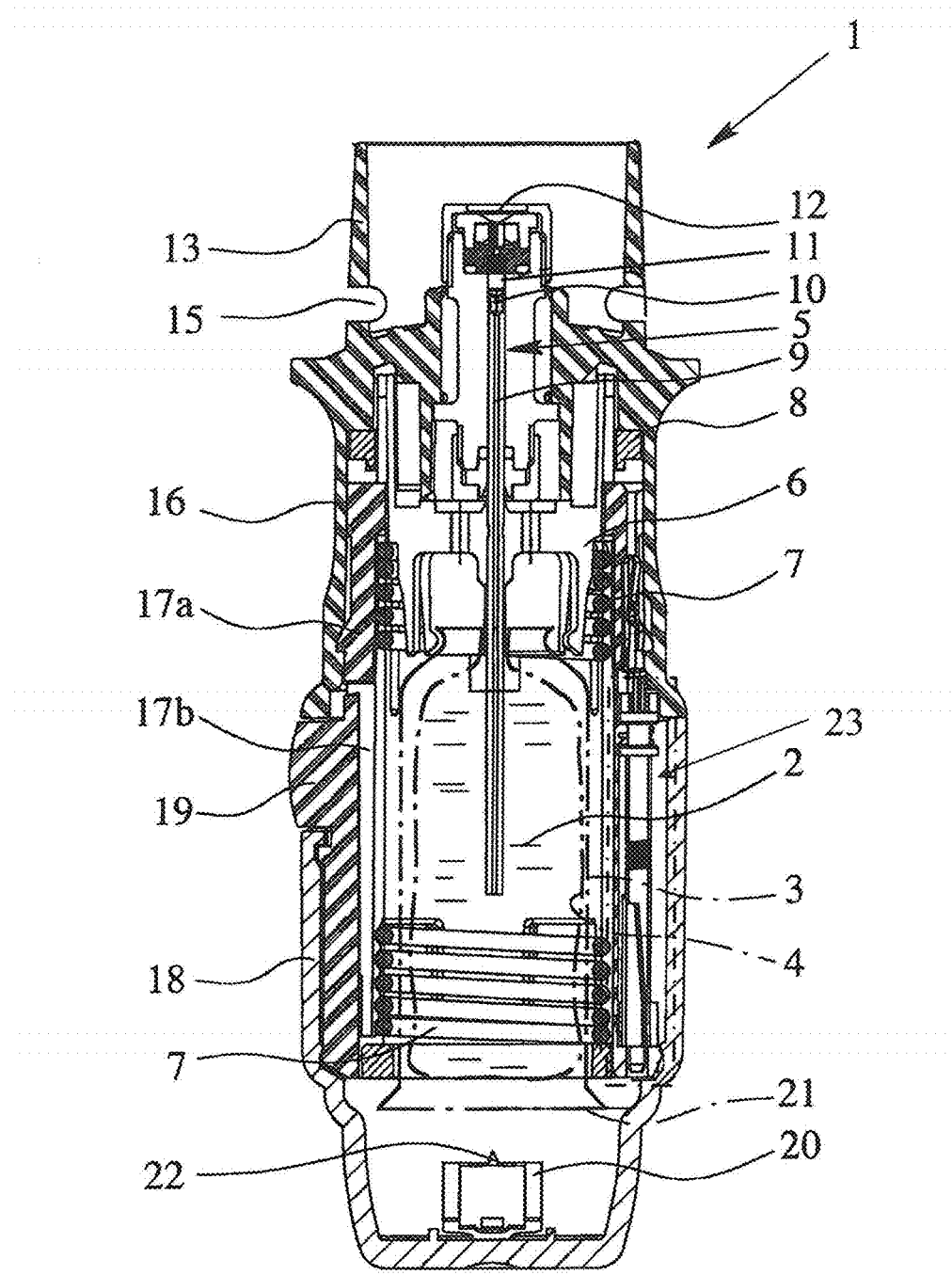
FIG. 1 is a schematic sectional view of a nebuliser according to the invention in its delivered state with a sealed container installed therein.
Figure 2:
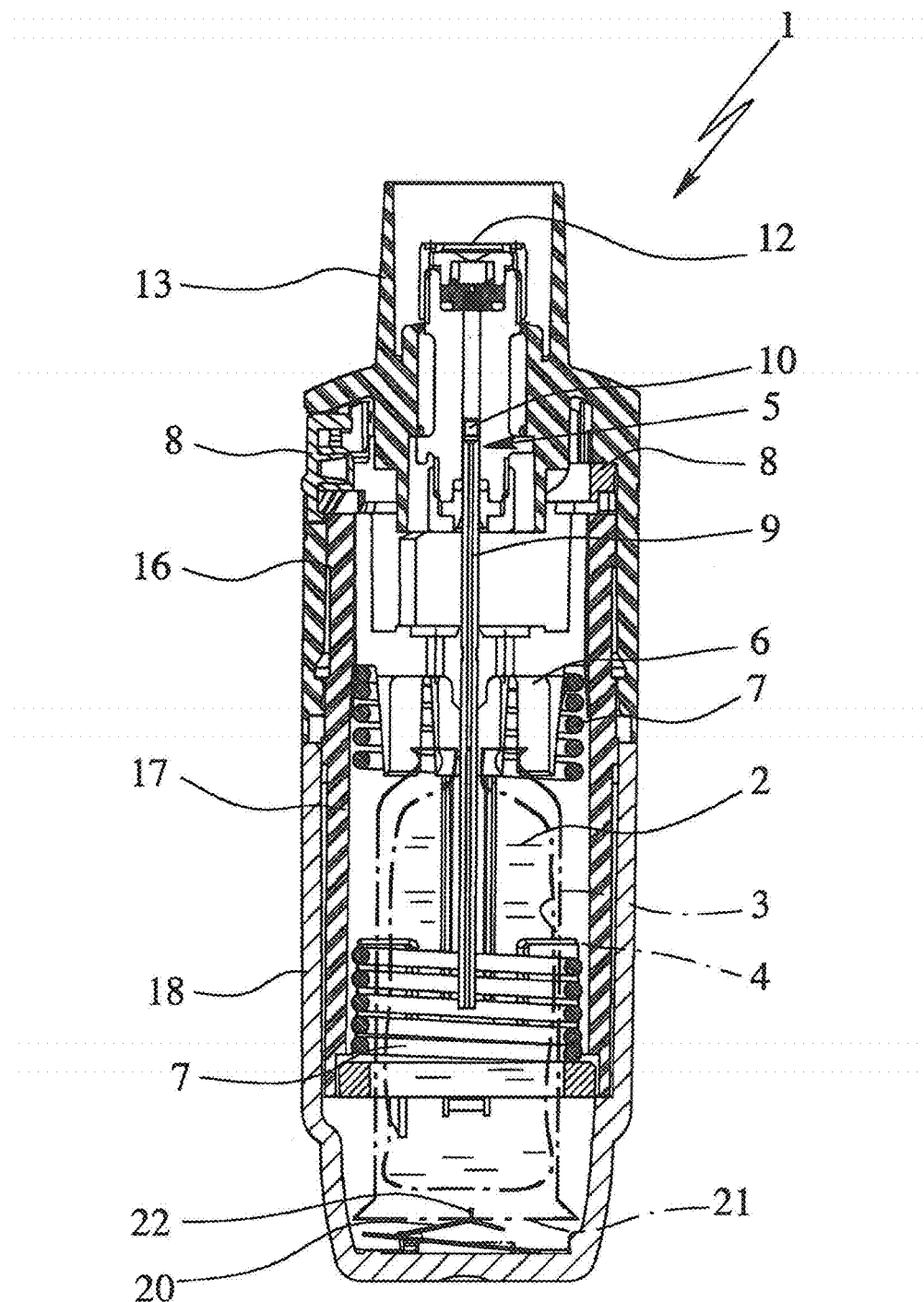
FIG. 2 is a schematic sectional view of the nebuliser according to FIG. 1 with the container opened.
Figure 3:
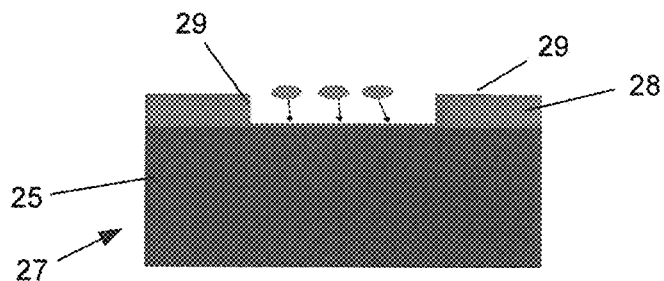
FIGS. 3 to 7 are partial views of a micronozzle of the nebuliser at different stages of production.
Figure 4:
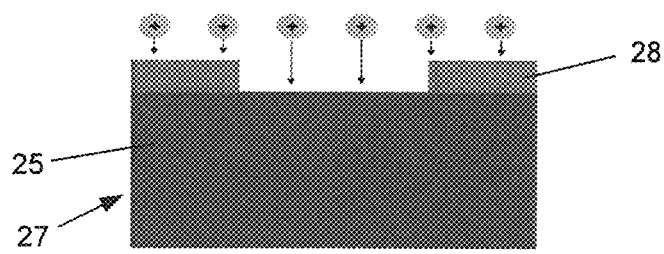
Figure 5:
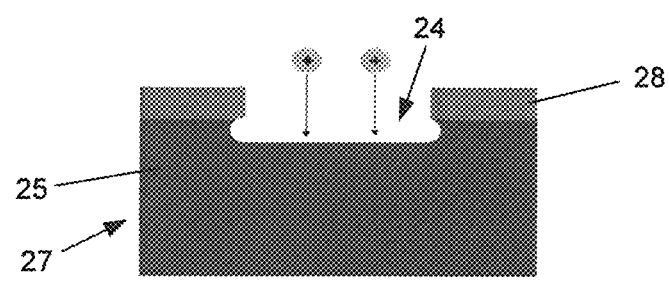
Figure 6:
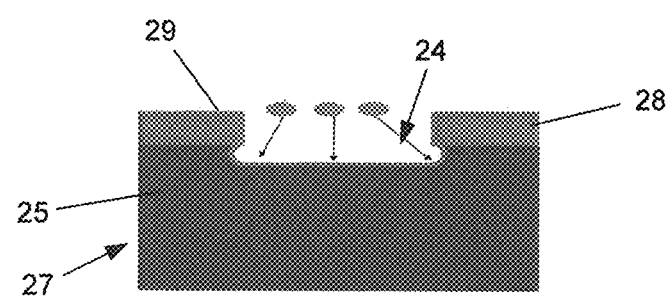
Figure 7:
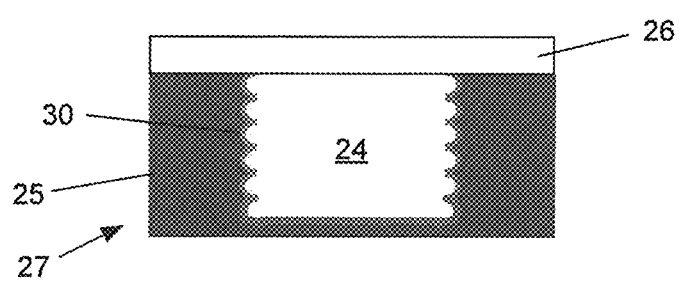

The nebuliser 1 for nebulising a fluid 2, particularly a potent medicament or the like, is embodied here as a portable inhaler and preferably operates without propellant gas. During nebulisation of the fluid 2, preferably a liquid, particularly an ethanolic or aqueous active substance formulation, a preferably respirable aerosol is formed which can be breathed in or inhaled by a user or patient. A container 3 of substantially cylindrical cross-section containing the fluid 2 is installed in the nebuliser 1, in particular so as to be replaceable, forming a reservoir for the fluid 2 that is to be nebulised, which is contained in a collapsible bag 4 in the container 3.

The nebuliser 1 further comprises a pressure generator 5 for delivering and nebulising the fluid 2 in a predetermined, optionally adjustable metered amount. The pressure generator 5 comprises a holder 6 for the container 3, a drive spring 7, a locking element 8 that can be released by manual actuation, a delivery tube 9 preferably embodied as a capillary, having a nonreturn valve 10 and an exit nozzle 12 comprising at least one micronozzle in the region of a mouthpiece 13. The container 3 is fixed in the metering device 1 via the holder 6 such that the delivery tube 9 extends into the container 3.

As the drive spring 7 is axially tensioned, the holder 6 is moved downwards with the container 3 and the delivery tube 9, and fluid 2 is drawn from the container 3 through the nonreturn valve 10 into a pressure chamber 11 of the pressure generator 5. During the subsequent relaxation of the drive spring 7, after the actuation of the locking element 8, the fluid 2 in the pressure chamber 11 is put under pressure, as the delivery tube 9 is moved back upwards by the relaxation of the drive spring 7, with the nonreturn valve 10 now closed, and acts as a pressure piston. This pressure drives the fluid 2 through the micronozzles of the exit nozzle 12, during which time it is nebulised to form the preferably respirable aerosol. The user inhales the aerosol, sucking supply air into the mouthpiece 13 through at least one supply air opening 15.

The metering device 1 comprises an upper housing part 16 and an inner housing part 17 rotatable relative thereto, having an upper part 17*a* and a lower part 17*b*, a lower housing part 18 being releasably attached to the inner housing part 17 by means of a manually operable retaining element 19. In order to insert or replace the container 3, the cap-like lower housing part 18 is detached from the nebuliser 1.

The lower housing part 18 can be rotated relative to the upper housing part 16, taking the lower part 17*b* of the inner housing part 17 with it. In this way the drive spring 7 is tensioned in the axial direction by means of a gear (not shown) acting on the holder 6. During the tensioning, the container 3 is moved axially downwards until the container 3 adopts its end position, in which the drive spring 7 is under tension. As the upper housing part 16 is rotated relative to the inner housing part 17 a spindle counting mechanism 23 is actuated.

When tension is applied for the first time, the container 3 is pierced or opened at its base, as an axially acting spring 20 mounted in the lower housing part 18 comes to abut on the container base 21, piercing the container 3 or a seal provided in its base with a piercing element 22, in order to ventilate it. During the nebulising process, the container 3 is moved axially upwards into its original position by the drive spring 7. The container 3 thus performs a lifting movement during the tensioning process and during the nebulising process.

The micronozzle essentially comprises a silicon plate 25 having trench-like depressions 24 in its surface, and a glass plate 26 covering the depressions 24 to form a channel system, this glass plate 26 being attached to the silicon plate 25 by anodic bonding.

During production, the depressions 24 are formed in the surface of a silicon wafer 27 by deep etching in various partial processes, in which first of all a masking layer 28 is applied, in order to determine the pattern of the depressions 24. In a first step, as shown in FIG. 3, a thin plasma polymer layer 29 with a thickness of a few nm is deposited and in a second step as shown in FIG. 4 this layer 29 is removed from the surfaces. In a third step, as shown in FIG. 5, isotropic etching is carried out, which is followed, in a fourth step shown in FIG. 6, by further deposition of a plasma polymer layer 29 to passivate the isotropically etched regions.

The steps are repeated until the depression 24 has the required depth. In a final step, after the required depth has been achieved, the plasma polymer is deposited in order to obtain a relatively thick protective layer 30 which far exceeds the thickness of the plasma polymer layer 29 for the passivation. The gas used to form the protective layer 30 is trifluoromethane ($CHF_3$), tetrafluoroethylene ($C_2F_4$) or octafluorocyclobutane (C$_4$F$_8$). After the removal of the masking layer the depressions 24 formed in the silicon plate 25 are closed off with the glass plate 26.

What is claimed is:

1. A method for producing a micro-nozzle having trench-like depressions (24) in the surface of a wafer (27) by plasma etching, comprising:
   (a) applying a plasma polymer layer of less than about 10 nm thick to respective portions of the wafer (27) to operate as a passivation layer;
   (b) etching the wafer (27) such that the passivation layer is removed and respective depth portions of the wafer (27), formerly under the passivation layer, are removed, thereby forming respective portions of the trench-like depressions (24) in the wafer (27);
   (c) applying a further plasma polymer layer of less than about 10 nm thick to respective surfaces within a plurality of the trench-like depressions (24), to operate as a further passivation layer;
   (d) etching the wafer (27) again such that the further passivation layer is removed and further respective depth portions of the wafer (27), formerly under the further passivation layer, are removed, thereby further forming the trench-like depressions (24) in the wafer (27);
   (e) repeating steps (c) through (d) a plurality of times until the trench-like depressions (24) are of a predetermined depth;
   (f) applying a final layer of polytetrafluoroethylene type material, greatly exceeding the thickness of the further passivation layer, to all surfaces of the wafer (27) within the plurality of the trench-like depressions (24) to operate as a protective layer (30).

2. The method according to claim 1, wherein the wafer (27) is made of silicon or glass.

3. The method according to claim 1, wherein the protective layer (30) is formed from the plasma polymer used for the passivation and its thickness is influenced by adjustment of the potential applied thereto.

4. The method according to claim 1, wherein the protective layer (30) is deposited before the stripping of a masking layer (28).

5. The method according to claim 4, wherein the protective layer (30) is deposited before the stripping of the masking layer (28) over the surface of the depressions (24).

6. The method according to claim 4, wherein after the stripping of the masking layer (28), the surface of the wafer (27) comprising the depressions (24) is attached to a glass plate (26) or a silicon plate by anodic bonding.

7. The method according to claim 6 wherein, the masking layer (28) is an oxide layer.

8. The method according to claim 6, wherein the protective layer (30) is deposited after the attachment of the wafer (27) to the glass plate (26) or the silicon plate, for which purpose the gas for the protective layer (30) is introduced into the depressions (24).

9. The method according to claim 1, wherein a gas used for the protective layer (30) is trifluoromethane (CHF3), tetrafluoroethylene (C2F4) octafluorocyclobutane (C4F8) or a mixture of these gases with an inert gas.

10. A micronozzle, comprising:
    a wafer (27), formed from a silicon plate (25) or a glass plate, comprising trench-like depressions (24) through one surface of, and into, the wafer (27),
    a cover, formed from a glass plate (26) or a silicon plate, covering the depressions (24), and which is attached to the wafer (27) by anodic bonding, and
    a protective layer (30) of polytetrafluoroethylene type material covering all surfaces of the wafer (27) within the depressions (24).

11. A nebuliser for dispensing a specified amount of a fluid as an aerosol, comprising:
    a micronozzle having:
    a wafer (27), formed from a silicon plate (25) or a glass plate, comprising trench-like depressions (24) through one surface of, and into, the wafer (27),
    a cover, formed from a glass plate (26) or a silicon plate, covering the depressions (24), and which is attached to the wafer (27) by anodic bonding, and
    a protective layer (30) of polytetrafluoroethylene type material covering all surfaces of the wafer (27) within the depressions (24).

12. The nebulizer according to claim 11, wherein the fluid comprises a medicament.

\* \* \* \* \*